United States Patent
Ichikawa

(10) Patent No.: US 9,445,891 B2
(45) Date of Patent: Sep. 20, 2016

(54) INTRAOCULAR LENS

(71) Applicant: CHUKYO MEDICAL CO., INC., Nagoya-shi, Aichi (JP)

(72) Inventor: Kazuo Ichikawa, Nagoya (JP)

(73) Assignee: CHUKYO MEDICAL CO., INC. (JP)

(*) Notice: Subject to any disclaimer, the term of this patent is extended or adjusted under 35 U.S.C. 154(b) by 0 days.

(21) Appl. No.: 14/260,991

(22) Filed: Apr. 24, 2014

(65) Prior Publication Data
US 2015/0305855 A1    Oct. 29, 2015

(51) Int. Cl.
*A61F 2/16*    (2006.01)

(52) U.S. Cl.
CPC .......... *A61F 2/16* (2013.01); *A61F 2002/1683* (2013.01)

(58) Field of Classification Search
CPC ........ A61F 2/163; A61F 2/16; A61F 2/1629; A61F 2002/1683
USPC ...................... 623/6.54, 6.38, 6.43
See application file for complete search history.

(56) References Cited

U.S. PATENT DOCUMENTS

| | | | |
|---|---|---|---|
| 4,327,450 A | 5/1982 | Girard | |
| 4,568,347 A * | 2/1986 | Reichert, Jr. | ................. 623/6.54 |
| 5,766,244 A * | 6/1998 | Binder | ...................... A61F 2/16 |
| | | | 623/6.54 |
| 6,899,733 B2 | 5/2005 | Snyder | |

FOREIGN PATENT DOCUMENTS

| | | | | |
|---|---|---|---|---|
| DE | 10 2009056810 | * | 6/2011 | ............... A61F 2/16 |
| JP | H05344990 A | | 12/1993 | |
| JP | H08501972 A | | 3/1996 | |
| JP | 2792588 B2 | | 9/1998 | |

\* cited by examiner

*Primary Examiner* — David H. Willse
*Assistant Examiner* — Tiffany Shipmon
(74) *Attorney, Agent, or Firm* — Bacon & Thomas, PLLC

(57) ABSTRACT

Provided is an intraocular lens including a lens and a pair of right and left loop-shaped support portions, and a folding-back portion is provided in the front end of each support portion. A sclera tunnel is formed in the circumferential direction at a position of a depth corresponding to the half of the thickness of the sclera in two symmetrical positions with respect to the visual axis in a portion adjacent to a limbus of the sclera. The front end of the support portion is extracted from the ciliary sulcus and is inserted into the sclera tunnel, so that the intraocular lens is fixed into the eye. Furthermore, at that time, the folding-back portion is hooked to a certain portion inside the sclera tunnel, so that the support portion is strongly restrained inside the sclera tunnel. As a result, the intraocular lens is more reliably fixed.

9 Claims, 4 Drawing Sheets

INTRAOCULAR LENS

BACKGROUND OF THE INVENTION

1. Field of the Invention

The present invention relates to an intraocular lens.

2. Description of the Related Art

As widely known, a surgery operation has been widely performed in which a cloudy white eye lens of a patient is extracted and an intraocular lens (IOL) is inserted into an eye as the treatment for the eye's cataract. For example, Japanese Patent No. 2792588 proposes an intraocular lens which is inserted into the eye from which the eye lens is extracted and is sutured to a ciliary body in the treatment of the cataract.

SUMMARY OF THE INVENTION

In the technique disclosed in Japanese Patent No. 2792588, the intraocular lens is sutured to the ciliary body (a method of suturing the intraocular lens). On the contrary, a method is also proposed which fixes an intraocular lens into a sclera without suturing (a method of fixing the intraocular lens into the sclera). In this method, for example, when a front end of a support portion of the intraocular lens is inserted into a tunnel-shaped hole portion formed inside the sclera in the circumferential direction, the tunnel strongly clamps the front end of the support portion so that the front end just stays inside the tunnel, and hence the intraocular lens is supported without suturing.

In this method, for example, there is no need to learn an intraocular lens suturing technique necessary for the method of suturing the intraocular lens. Further, it is reported that, when this method is used, the intraocular lens may be disposed at the center position of the eye with high precision so as to improve the lens fixing stability (particularly, the axial stability of the lens) and hence an effect is obtained in which the lens is not easily inclined.

The method of fixing the intraocular lens into the sclera has an advantage that the method may be applied to the existing intraocular lens without any modification. Certainly, there is an advantage in that the existing intraocular lens may be directly used. In contrast, the intraocular lens appropriate (or specialized) for the fixation into the sclera is not sufficiently developed.

Although it is reported that the intraocular lens is effectively supported by the above-described method of fixing the intraocular lens into the sclera, when the support portion may be reliably fixed into the sclera tunnel, for example, by changing the shape of the support portion of the intraocular lens as the shape appropriate for the method of fixing the intraocular lens into the sclera, there is a possibility that the method of fixing the intraocular lens into the sclera becomes more excellent. This challenge is not limited to the method of fixing the intraocular lens into the sclera, and also corresponds to the challenge for all treatments of fixing the intraocular lens to a part of the sclera like the outer surface of the sclera.

Therefore, an object of the invention is to provide an intraocular lens suitable for a treatment of inserting a support portion from a ciliary sulcus to be fixed to a sclera and reliably fixed without suturing by a treatment of inserting the intraocular lens into an eye from which an eye lens is extracted from a ciliary sulcus to be fixed to a sclera.

In order to solve the above-described problems, according to the invention, there is provided an intraocular lens including: a lens portion that is disposed at a rear section of an eye from which at least a part of an eye lens is extracted and carries out a lens function of the eye lens; and a support portion that has a front end extending in the circumferential direction while extending in a leg shape outward in the radial direction involving with a visual axis from a limbus of the lens portion and fixes the lens portion to the rear section while the front end is inserted from a ciliary sulcus, wherein the portion of the support portion inserted from the ciliary sulcus has a folding-back portion that has a shape in which the portion is folded back so as to return in the opposite direction to the extension direction from the lens portion and is hooked to a part of a sclera. Accordingly, since the folding-back portion that is inserted from the ciliary sulcus into the sclera is hooked to a certain portion inside the sclera, the support portion is strongly restrained inside the sclera. Accordingly, the intraocular lens is reliably fixed. Further, the intraocular lens may be disposed at an appropriate position in the rear section while being inserted from the ciliary sulcus.

The folding-back portion may be folded back at an angle at which the folding-back portion is insertable into a tunnel-shaped hole portion formed inside the sclera along with a part of the support portion other than the folding-back portion. Accordingly, since the folding-back portion is insertable into the tunnel-shaped hole portion formed inside the sclera, the support portion is strongly restrained inside the sclera in a manner such that the folding-back portion inserted into the sclera is hooked to a certain portion inside the sclera. Thus, the intraocular lens is reliably fixed.

Further, when the folding-back portion is inserted into a tunnel-shaped hole portion formed inside the sclera along with a part of the support portion other than the folding-back portion, the length of the folding-back portion may be adjusted to the length in which the entire folding-back portion is accommodated inside the hole portion. Accordingly, since the entire folding-back portion may be accommodated in the tunnel-shaped hole portion formed inside the sclera, the support portion is strongly restrained inside the sclera in a manner such that the folding-back portion inserted into the sclera is hooked to a certain portion inside the sclera. Thus, the intraocular lens is reliably fixed.

Further, the support portion may be formed so that the folding-back portion is hooked to an outer surface of the sclera while the lens portion is disposed at the rear section. Accordingly, the intraocular lens may be reliably fixed into the eye in a manner such that the folding-back portion is hooked to the outer surface of the sclera.

Further, the support portion may be formed in a plurality of loop shapes extending from the limbus of the lens portion so as to be symmetrical to each other with respect to the visual axis, and the folding-back portion may be formed in each of the front ends of all support portions. Accordingly, since the plurality of loop-shaped support portions are strongly restrained inside the sclera by the folding-back portions of the front ends, the intraocular lens may be reliably fixed.

Further, the support portions may be formed in two loop shapes extending from the limbus of the lens portion so as to be symmetrical to each other with respect to the visual axis and the folding-back portion may be formed in the front ends of two support portions. Accordingly, since two loop-shaped support portions are strongly restrained inside the sclera by the folding-back portions of the front ends, the intraocular lens may be reliably fixed.

Further, scale marks may be marked on the folding-back portion at an interval in the longitudinal direction. Accordingly, since the folding-back portion may be easily separated by bending using the scale marks, the length of the folding-back portion may be simply adjusted to an appropriate length.

DETAILED DESCRIPTION OF THE PREFERRED EMBODIMENTS

Figure 1:
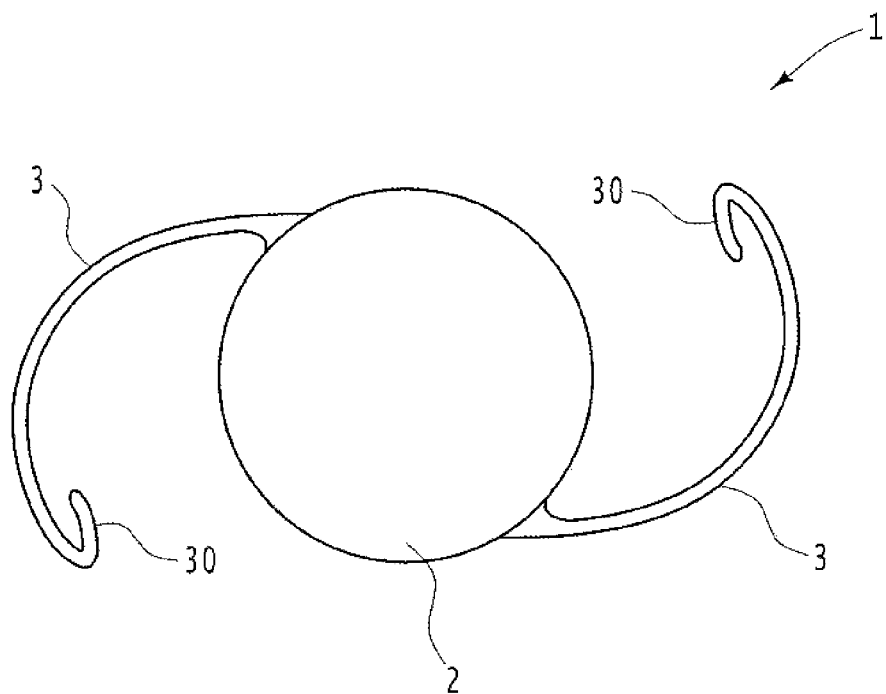
FIG. 1 is a front view illustrating an embodiment of an intraocular lens of the invention.
Figure 2:
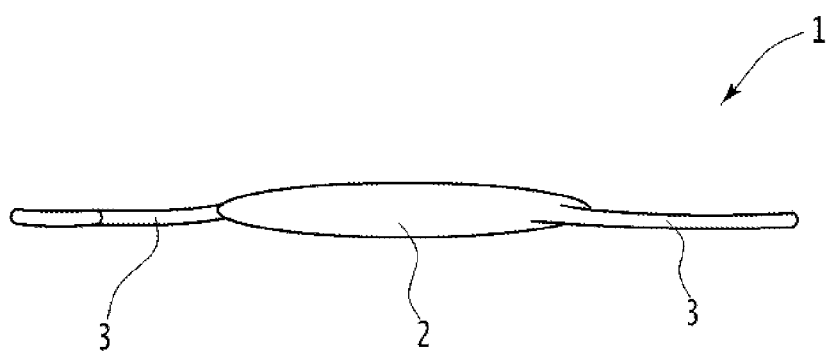
FIG. 2 is a side view illustrating the intraocular lens of FIG. 1.
Figure 3:
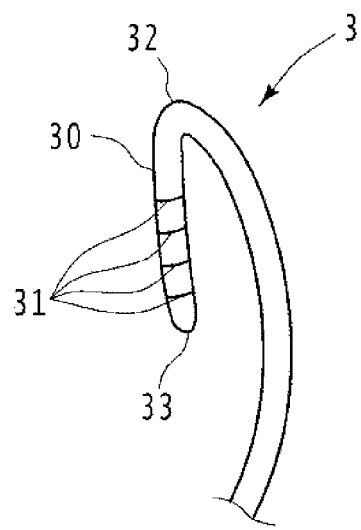
FIG. 3 is a view illustrating a front end of the intraocular lens.

Hereinafter, an embodiment of the invention will be described by referring to the drawings. First, FIGS. 1 to 3 illustrate an intraocular lens 1 of an embodiment of the invention. FIG. 1 is a front view of the intraocular lens 1, and FIG. 2 is a side view thereof (the description on the direction of the side surface, the front surface, or the like indicates the direction (the side surface, the front surface, or the like) in a face (or an eye) of a patient having an eye into which the intraocular lens is fixed).

The intraocular lens 1 mainly includes a lens 2 and a support portion 3. For example, the lens 2 is disposed at the rear section (or an eye rear section, that is, an area behind the iris) after an eye lens which becomes cloudy white due to the cataract is extracted (entirely or partially extracted) from the patient's eye so that the lens carries out the lens function of the extracted eye lens.

The support portion 3 is a portion that supports the lens 2 to the rear section. As illustrated in FIG. 1 and the like, the support portion 3 extends from two positions of the limbus of the lens 2 so as to have a pair of loop shapes (or leg shapes or haptic shapes), and has a line-symmetric shape with respect to the visual axis (the center axis of the lens 2). For example, the loop shape is a curve shape which extends in the circumferential direction (particularly, at the front end side thereof) while extending outward in the radial direction involving with the visual axis.

As illustrated in FIG. 2, the shape obtained when viewed from the lateral side of the support portion 3 may be, for example, a shape substantially included in the same plane as that of the lens 3. Alternatively, the shape obtained when viewed from the lateral side of the support portion 3 may be formed so that the support portion obliquely extends in a direction from the limbus of the lens 3 toward the front or rear side of the inside of the eye.

The intraocular lens 1 of the invention may be formed of the same material as the material (for example, PMMA or the like) of the existing intraocular lens. Accordingly, the intraocular lens 1 has flexibility (elasticity and bendability), and hence may be inserted into the eye in the form of, for example, a bar shape by the use of an injector or the like. The support portion 3 may be formed of, for example, a resin material or the like so as to be integrated with the lens 2.

Alternatively, the support portion may be formed separately from the lens 2, and then may be bonded (attached) to each other.

As the main part of the invention, the intraocular lens 1 includes a folding-back portion 30 which is formed at the front end side of the support portion 3 so as to extend in the folding-back direction. The folding-back shape of the folding-back portion 30 may be formed in a folding-back shape with a corner or a curved folding-back shape without a corner.

As described above, the support portion 3 has elasticity. For example, in a natural state (that is, a state where no external force is exerted), the folding-back portion 30 and the other portion may be separated from each other as illustrated in FIG. 3 and the like. In this case, when the folding-back portion 30 is folded back (that is, when the folding-back portion 30 is folded back so as to overlap the other support portion 3 in one linear shape), an elastic restoration force is exerted so that the folding-back portion 30 and the other portion are separated from each other as illustrated in FIG. 3. Alternatively, the folding-back portion of the front end of the support portion 3 may not have sufficient elasticity as described above and may be maintained in the shape of FIG. 3 at all times.

Figure 4:
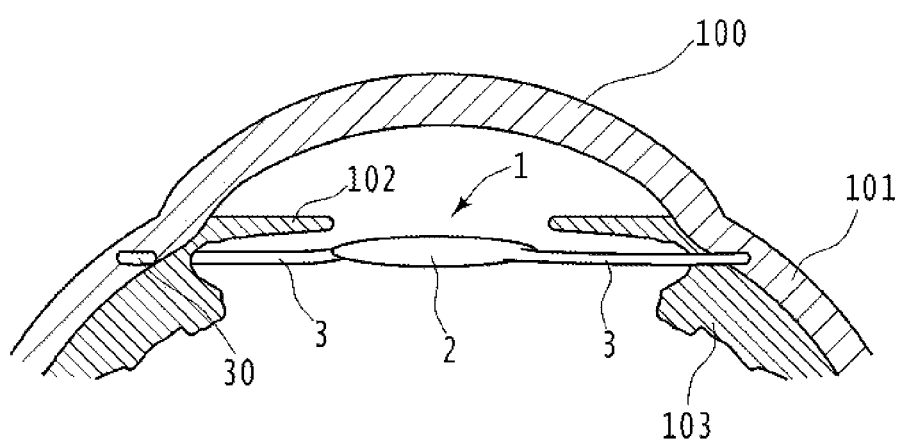
FIG. 4 is a view illustrating a state where the intraocular lens is inserted and fixed into an eye.

FIG. 4 illustrates the detail of the folding-back portion 30. The folding-back portion 30 is folded back at a bent portion 32, and a folding-back-side front end 33 faces the opposite direction with respect to the extension direction of the support portion 3. The folding-back portion in the bent portion 32 may be a folding-back portion with a corner or a curved folding-back portion without a corner as described above. However, a configuration may be employed in which the folding-back angle of the bent portion 32 is not set to too large and is set to an angle at which the folding-back portion 30 and the other support portion 3 are insertable into the sclera tunnel by using the bent portion 32 as the leading portion as will be described later.

For example, scale marks 31 are marked on the folding-back portion 30 at an interval in the longitudinal direction by printing. As illustrated in FIG. 4, a plurality of the scale marks 31 may be provided, and the interval of the scale marks 31 may be the same interval of, for example, 0.5 mm or the like. Furthermore, one scale mark 31 may be provided.

Since the support portion of the intraocular lens 1 is formed of the same material as that of the existing intraocular lens, the folding-back portion 30 is comparatively easily separated at the bent portion when the folding-back portion 30 is bent at an arbitrary position by an operator using an appropriate medical instrument. Accordingly, when the operator bends the folding-back portion 30 at a position of an appropriate length based on the scale marks 31, the length of the folding-back portion 30 may be simply adjusted. Thus, the length of the folding-back portion 30 may be set to an appropriate length in response to the length of the sclera tunnel to be described later.

FIG. 4 illustrates an example of a state where the intraocular lens 1 is transplanted (attached) into the eye. Then, an example of the halfway operation is illustrated in FIGS. 5 and 6.

For example, the intraocular lens 1 of the invention is fixed to the rear section (the eye rear section) inside the eye from which the eye lens that becomes cloudy white due to the cataract is entirely or partially extracted by the fixation method (without suturing) inside the sclera. As illustrated in FIG. 4, the folding-back portions 30 of the pair of right and left support portions 3 of the lens 2 illustrated in the drawings are buried inside a sclera 101 while the lens 2 is disposed behind an iris 102. FIG. 4 illustrates a case where the eye lens is entirely extracted.

The sequence of the intraocular lens transplanting operation of the invention may be set as, for example, the sequence shown in the document (Journal of Cataract and Refractive Surgery, vol. 34, pp. 1433-1438 (2008)) of Amar Agarwal or the like, and an example thereof is shown as below.

Figure 5:
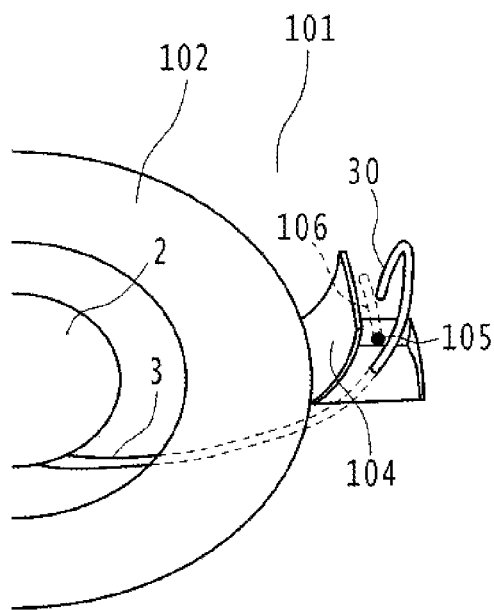
FIG. 5 is a view illustrating a first example of a halfway state of an intraocular lens transplanting operation.
Figure 6:
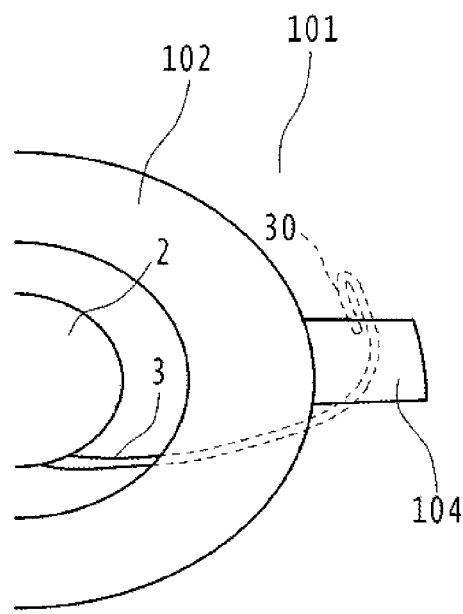
FIG. 6 is a view illustrating a second example of a halfway state of an intraocular lens transplanting operation.

After the conjunctiva excision or the like, a sclera-half-layer valve 104 which is a valve having a thickness substantially half of the thickness of the sclera is formed at a position adjacent to a limbus of a cornea 100 in the sclera 101 as illustrated in FIG. 5. The position of forming the sclera-half-layer valve 104 is set as two symmetrical positions involving with the visual axis at a position adjacent to the limbus in the sclera surface. FIG. 5 illustrates one of two sclera-half-layer valves 104 formed in this way.

Then, a sclerotomy is formed in a direction from one position of the lower layer of the sclera-half-layer valve 104 of the sclera 101 toward, for example, the center of the eye ball (or a direction toward the ciliary sulcus and the ciliary body flat portion). In addition, a sclera tunnel 106 is formed in a direction substantially parallel to the limbus, that is, the circumferential direction involving with the visual axis by using a position 105 serving as an entrance and substantially located at, for example, the half depth of the sclera thickness from the sclera surface in the side wall of the portion where the sclera-half-layer valve 104 is perforated. The sclera tunnel 106 may be formed so as to perforate the sclera surface as an exit while having an appropriate length (for example, 2 mm to 3 mm).

Then, the intraocular lens 1 is inserted into the eye by a predetermined injector or the like, for example, while being rolled in a bar shape from the incision formed in the cornea 100. During the insertion, one support portion 3 is located at the head side and the other support portion 3 is located at the tail side. Even when the head-side support portion 3 and the lens 2 are inserted into the eye, the tail-side support portion 3 is made so that a part of the tail-side support portion 3 is exposed to the outside from the incision of the cornea 100.

As illustrated in FIG. 5, in a state where the sclera-half-layer valve 104 is opened, the front end (for example, the folding-back portion 30) of the head-side support portion 3 inserted into the eye is drawn from the rear section through the sclerotomy by, for example, an instrument such as 25-g forceps so as to be exposed to the outside of the eye from the lower portion of the sclera-half-layer valve 104. At that time, the entire folding-back portion 30 is exposed to the outside of the eye.

Then, the folding-back portion 30 that is exposed to the eye is inserted into the sclera tunnel 106. In this sequence, for example, an instrument such as a 25-g forceps may be used as described above. In this insertion, the bent portion 32 is inserted as a head portion.

In order to enable this insertion, the folding-back angle of the bent portion 32 may be set to an angle at which the bent portion is insertable into the sclera tunnel 106 along with a part of the support portion 3 other than the folding-back portion. Then, the length of the folding-back portion may be set to the length at which the entire folding-back portion is accommodated in the tunnel-shaped hole portion formed inside the sclera along with a part of the support portion 3 other than the folding-back portion. As described above, the operator sets the length of the folding-back portion 30 to an appropriate length in advance based on the scale marks 31.

The folding-back portion 30 is inserted until the folding-back-side front end 33 enters the sclera tunnel 106, that is, the entire folding-back portion 30 is accommodated in the sclera tunnel 106. Accordingly, both the bent portion 32 and the folding-back-side front end 33 are accommodated in the sclera tunnel 106. The same sequence is performed on the other support portion 3. Accordingly, the front ends including the folding-back portions 30 are accommodated inside the sclera tunnel 106 while two support portions 3 are located at the symmetrical positions with respect to the visual axis.

When the above-described sequence ends, two sclera-half-layer valves 104 are closed. At that time, for example, fiblin glue is applied to (the rear surface) of the sclera-half-layer valve 104 or the opposite surface thereof so that the sclera-half-layer valve 104 is stuck to the sclera 101. The above-described example is an example of a main sequence of fixing the intraocular lens into the sclera. By the above-described sequence, the sclera tunnel 106 strongly clamps the support portion 3 so that the support portion 3 is restrained and held inside the sclera tunnel 106. As a result, the intraocular lens 1 is fixed into the eye without suturing.

Alternatively, the intraocular lens 1 of the invention may be transplanted into the eye by the method disclosed in the document (Journal of Cataract and Refractive Surgery, vol. 33, pp. 1851-1854 (2007)) of Gabor B. Scharioth or the like.

In this method, a sclerotomy is formed from the surface of the sclera 101 toward the rear section without forming the sclera-half-layer valve 104. Then, the sclera tunnel (the hole portion) 106 having an appropriate length (for example, 2 to 3 mm) is formed from the position substantially corresponding to the half of the thickness of the sclera in the sclerotomy in a direction substantially parallel to the limbus, that is, the circumferential direction involving with the visual axis by using the sclera surface as an exit.

Then, as described above, the support portion 3 is inserted into the sclera tunnel 106 along with the folding-back portion 30. In this case, the sclerotomy may be sutured if necessary after the front end is inserted into the sclera tunnel. Furthermore, the method of transplanting the intraocular lens 1 of the invention into the eye is not limited to the methods of two documents above, and any method of fixing the intraocular lens into the sclera may be used.

In the invention, the folding-back portion 30 has the following effect. In a case where the folding-back portion (particularly, the folding-back part) 30 has sufficient elasticity, when the folding-back portion 30 is inserted into the sclera tunnel 106 in the above-described sequence, the folding-back portion may be inserted so as to overlap the other portion of the support portion 3 in a linear shape according to the above-described sequence. When the folding-back portion is accommodated inside the sclera tunnel 106, the folding-back portion 30 is opened again by its elastic restoration force, and presses the inner wall of the sclera tunnel 106.

Thus, a case may be supposed in which the inner wall of the sclera tunnel 106 is stretched. However, the front end including the folding-back portion 30 is pressed back from the outside by the strength of the sclera after the inner wall is stretched. Accordingly, the pressing force and the pressing-back force are equalized. Due to the existence of the tension state, the front end including the folding-back portion 30 does not easily move inside the sclera tunnel 106.

In addition, in a case where a force is exerted so that the support portion 3 comes out of the entrance 105 of the sclera tunnel 106, the folding-back-side front end 33 is held (hooked (engaged)) by a certain portion of the inner wall of the sclera tunnel 106, and hence it is possible to strongly prevent the support portion 3 from coming out of the sclera tunnel 106. By the above-described action, the intraocular lens 1 is reliably fixed into the eye.

Furthermore, the bent portion 32 may not have elasticity capable of folding (the folding-back part) of the folding-back portion 30. In that case, the folding-back portion 30 is inserted into the sclera tunnel 106 in a natural shape so as to expand the sclera tunnel 106 while not being folded.

Even in this case, when a force is exerted so that the folding-back portion 30 presses the inner wall of the sclera tunnel 106 and the folding-back portion 30 is drawn out of the entrance 105, the front end of the folding-back portion 30 is hooked to a certain portion of the inner wall of the sclera tunnel 106. Thus, it is possible to strongly suppress the support portion 3 from moving inside the sclera tunnel 106 and hence to reliably fix the intraocular lens 1 into the eye.

The above-described embodiment may be modified within the scope of the spirit of claims. For example, in the above-described embodiment, two support portions are provided, but the invention is not limited thereto. For example, three, four, five, or six support portions may be provided other than two support portions. Further, in the above-described example, the support portion is formed in a loop shape, but may be formed in a shape in which the front end extends in a leg shape outward in the radial direction involving with the visual axis from the limbus of the lens 2 or a shape in which the front end extends in the circumferential direction other than the loop shape.

Further, the folding-back direction of the folding-back portion 30 is set so that the folding-back portion is folded back inward (toward the center of the lens 2) in the example of FIG. 1, but may be folded back outward. However, the folding-back portion may be folded back in the other directions, that is, a direction intersecting a plane including the support portion 3 (or the lens 2).

Figure 7:
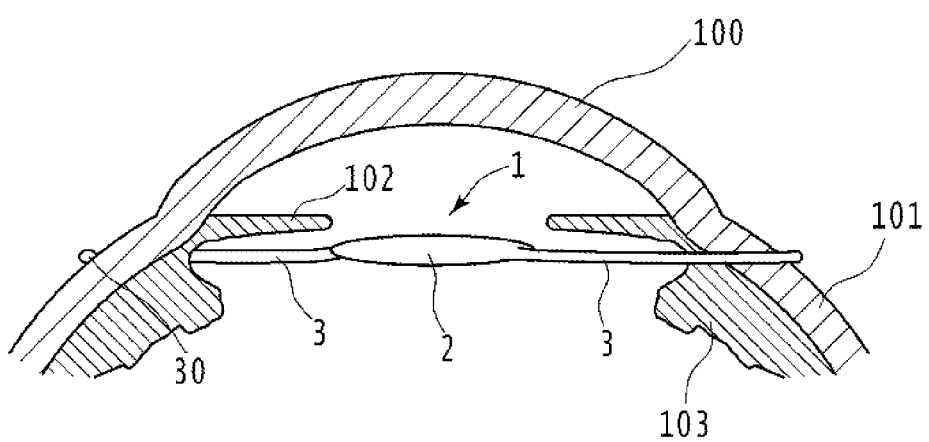
FIG. 7 is a view illustrating an example in which the intraocular lens is fixed to the outside of a sclera.

In the above-described example, a tunnel is formed inside the sclera, and the support portion including the folding-back portion 30 is inserted thereinto. However, in the invention, the support portion may be fixed to a position different from the inside of the sclera as long as the support portion is inserted from the ciliary sulcus. For example, FIG. 7 illustrates an example in which the support portion is fixed to the outer surface of the sclera. In this example, the support portion 3 including the folding-back portion 30 is drawn to the outside of the sclera 101 from the ciliary sulcus 104 so that the folding-back portion 30 is hooked to the outer surface of the sclera 101. In this example, for example, the sclera-half-layer valve 104 may not be formed.

In a case where a force of pulling the support portion 3 into the eye is exerted when the support portion 3 is drawn to the outside of the sclera 101, it is possible to resist the pulling force in a manner such that the folding-back portion 30 is hooked to the outer surface of the sclera 101. Thus, since the slipping of the support portion 3 is suppressed by the folding-back portion 30, the intraocular lens 1 is reliably fixed into the eye. In this example, the length of the support portion 3 may be set to an appropriate length in which the entire folding-back portion 30 is drawn to the outside of the sclera 101. Similarly, in the example of FIG. 4 or the like, the length of the support portion 3 may be set to an appropriate length in which the entire folding-back portion 30 is inserted into the sclera 101.

What is claimed is:
1. An intraocular lens comprising:
a lens portion that is disposed at a rear section of an eye from which at least a part of an eye lens is extracted and carries out a lens function of the eye lens; and
a support portion having a continuous curve shape with a front end extending in the circumferential direction while extending in a leg shape outward in the radial direction involving with a visual axis from a limbus of the lens portion and fixes the lens portion to the rear section while the front end is inserted from a ciliary sulcus,
wherein the portion of the support portion inserted from the ciliary sulcus has a folding-back portion that has a shape in which the portion is folded back so as to return in the opposite direction to the extension direction from the lens portion and is adapted to be hooked to a part of a sclera for restraining the support portion inside the sclera, and
wherein the folding-back portion has a folding-back-side front end facing the opposite direction with respect to the extension direction of the support portion.
2. The intraocular lens according to claim 1,
wherein the folding-back portion is folded back at an angle at which the folding-back portion is insertable into a tunnel-shaped hole portion formed inside the sclera along with a part of the support portion other that the folding-back portion.
3. The intraocular lens according to claim 1,
wherein when the folding-back portion is inserted into a tunnel-shaped hold portion formed inside the sclera along with a part of the support portion other than the folding-back portion, the length of the folding-back portion is adjustable to the length in which the entire folding-back portion is accommodated inside the hole portion.
4. The intraocular lens according to claim 1,
wherein the support portion is formed so that the folding-back portion is hooked to an outer surface of the sclera while the lens portion is disposed at the rear section.
5. The intraocular lens according to claim 4, in which a pair of support portions extend from two position of the limbus of the lens and so as to have a pair of loops and folding-back portions adapted to be hooked to the sclera.
6. The intraocular lens according to claim 1, wherein the support portion extends in a direction substantially included in the same plane as that of the lens such that the shape of the support portion obtained when viewed from the lateral side of the support portion is substantially included in the same plane as that of the lens.
7. The intraocular lens according to claim 6, in which a pair of support portions extend from two position of the limbus of the lens and so as to have a pair of loops and folding-back portions adapted to be hooked to the sclera.
8. The intraocular lens according to claim 1, further comprising scale marks on the folding-back portion at an interval in the longitudinal direction.
9. The intraocular lens according to claim 1, in which a pair of support portions extend from two position of the limbus of the lens and so as to have a pair of loops and folding-back portions adapted to be hooked to the sclera.

* * * * *